United States Patent [19]

Yale et al.

[11] 3,957,787

[45] May 18, 1976

[54] 1,2-DIHYDRO-2-IMINO-1-(BROMO-PHENYLALKYL)PYRIMIDINES

[75] Inventors: Harry Louis Yale, New Brunswick, N.J.; Ramesh B. Petigara, Lansdale, Pa.

[73] Assignee: E. R. Squibb & Sons, Inc., Princeton, N.J.

[22] Filed: Dec. 16, 1974

[21] Appl. No.: 532,796

Related U.S. Application Data

[62] Division of Ser. No. 382,804, July 26, 1973, Pat. No. 3,868,374.

[52] U.S. Cl. ............... 260/256.4 H; 260/256.4 F; 260/256.4 B; 260/256.4 C; 260/256.4 N; 260/256.5 R; 424/251
[51] Int. Cl.² ............... C07D 239/30; C07D 239/42
[58] Field of Search ............... 260/256.4 H, 256.5 R Primary Examiner—Raymond V. Rush
Assistant Examiner—James H. Turnipseed
Attorney, Agent, or Firm—Lawrence S. Levinson; Merle J. Smith; Burton Rodney

[57] ABSTRACT

Compounds of the formula

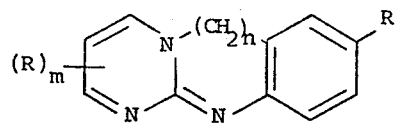

exhibit central nervous system stimulating properties and act as muscle relaxants.

3 Claims, No Drawings

1,2-DIHYDRO-2-IMINO-1-(BROMOPHENYLALKYL)PYRIMIDINES

This is a division of application Ser. No. 382,804, filed July 26, 1973, now U.S. Pat. No. 3,868,374.

OBJECTS OF THE INVENTION

It is an object of the present invention to provide new compounds having central nervous system (CNS) stimulating activity. Another object is to provide new compounds having muscle relaxant properties. A further object is to provide intermediates for the preparation of the final compounds of the invention. Yet another object is to provide a method for the preparation of both the intermediate and the final compounds of the present invention. Still another object is to provide a method for the administration of the final compounds of the invention. A still further object is to provide pharmaceutical compositions containing as active ingredients the final compounds of the present invention. These and other objects of the present invention will be apparent from the following description.

SUMMARY OF THE INVENTION

The compounds of the present invention have the following formula

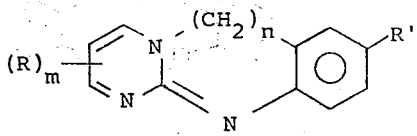

wherein $m$ may be 1 or 2; when m is 1, R occupies either the 4- or 5- positions of the original 2-aminopyrimidine, but when R is halogen, it occupies only position-5; when $m$ is 2, the two R-substituents occupy the 4- and 5-positions of the original 2-aminopyrimidine, but only one of the two R-substituents can be halogen and it must occupy the 5-position;

R may be the same or different and may be hydrogen, halogen (F, Cl, or Br), alkyl of from 1 to 4 carbons, benzyl, phenyl, or mono-substituted phenyl wherein the substituent may be halogen (F, Cl, Br or I), alkyl of from 1 to 4 carbons, alkoxy of from 1 to 4 carbons, or trifluoromethyl;

R' may be hydrogen, halogen (F, Cl, Br or I), alkyl of from 1 to 4 carbons, alkoxy of from 1 to 4 carbons, alkylthio of from 1 to 4 carbons, alkylsulfonyl wherein the alkyl radical has from 1 to 4 carbons, phenyl, phenyloxy, sulfamoyl, dialkylamidosulfonyl wherein each alkyl radical may have from 1 to 4 carbons, trifluoromethyl, mono-substituted phenyl or mono-substituted phenyloxy wherein the substituent may be halogen (F, Cl, Br or I), alkyl of from 1 to 4 carbons, alkoxy of from 1 to 4 carbons or trifluoromethyl; $n$ is 2 or 3, and pharmaceutically acceptable acid addition salts thereof.

The foregoing compounds possess central nervous system stimulating properties and act as muscle relaxants.

DETAILED DESCRIPTION

The final compound I of the present invention may be prepared by reacting a 2-aminopyrimidine II with an o-bromophenalkylene bromide III. This reaction takes place in any solvent or solvent mixture in which the reactants can be dissolved and which has a boiling point of at least about 100°C. Typical solvents are aromatic hydrocarbons, ethers, aliphatic alcohols or aryl-substituted aliphatic alcohols. Toluene and xylene are examples of suitable aromatic hydrocarbons. Monomethyl ether of diethylene glycol, dimethyl ether of diethylene glycol (diglyme), monomethyl ether of ethylene glycol or dimethyl ether of ethylene glycol (glyme) are examples of suitable ethers. n-Amyl alcohol is an example of a suitable aliphatic alcohol, while benzyl alcohol is an example of a suitable aryl-substituted aliphatic alcohol. Heating compounds II and III in a solvent as described above, or a mixture thereof, at temperatures from about 100° to about 140°C for a period of several hours, typically from about 3 to about 24 hours produces a pyrimidinium compound IV. The latter is converted to an imino compound V by treating with a water miscible alcohol and an alkali metal alkoxide of up to 3 carbon atoms. The reaction takes place at room temperature over a period of from about 1 to about 4 hours. Compound V may be converted to the final compound I by treating with a water miscible alcohol and an alkali metal alkoxide of up to 3 carbons in the presence of copper at a temperature of from about 60° to about 120° for several days, typically from about 4 to about 10 days. Alternatively, IV may be converted directly to I by heating at a temperature of from about 60°C to about 120°C for about 4 to 10 days, typically from about 6 to about 8 days in the presence of potassium carbonate and copper in a solvent such as dimethylformamide, dimethylacetamide, dichlorobenzene, trichlorobenzene, or diethylbenzene. Preferably, however, IV may be converted directly to I by heating at a temperature of from about 60° to about 120°C for about 4 to 10 days, typically from about 6 to about 8 days in the presence of an alkali metal hydroxide, alkali metal carbonate, tris-alkali metal phosphate, alkali metal metaborate or alkali metal tetraborate in a solvent comprising a mixture of water and a water miscible alcohol in the presence of copper. Specific examples of suitable compounds include LiOH, NaOH, KOH, RbOH, CsOH, $Na_2CO_3$, $K_2CO_3$, $Rb_2CO_3$, $Cs_2CO_3$, $Na_3PO_4$, $K_3PO_4$, $Rb_3PO_4$, $Cs_3PO_4$, $Na_2B_2O_4$, $Na_2B_4O_7$, $K_2B_2O_4$, and $K_2B_4O_7$. The ratios of water and alcohol in the mixture of water and a water miscible alcohol are such that a homogeneous single phase system results.

When $m$ is 1, and when R occupies only the 5-position of II and R' occupies only the 5-position (para to the bromine atom) of III, only one isomer, I, is formed. When $m$ is 1, and when R occupies only the 4-position of II$a$, and R' occupies only the 5-position of III, two isomers, I$a$ and I$b$ are formed via the intermediates IV$a$ and V$a$ and IV$b$ and V$b$, respectively. When m is 2, and since the two R's occupy only the 4-, 5-positions and R' occupies only the 5-position of III, two isomeric products, I$a$ and I$b$ are formed. These isomers, in all instances, can be separated by conventional procedures, e.g., fractional recrystallization or column chromatography.

The foregoing reaction sequence is illustrated by the following equations:

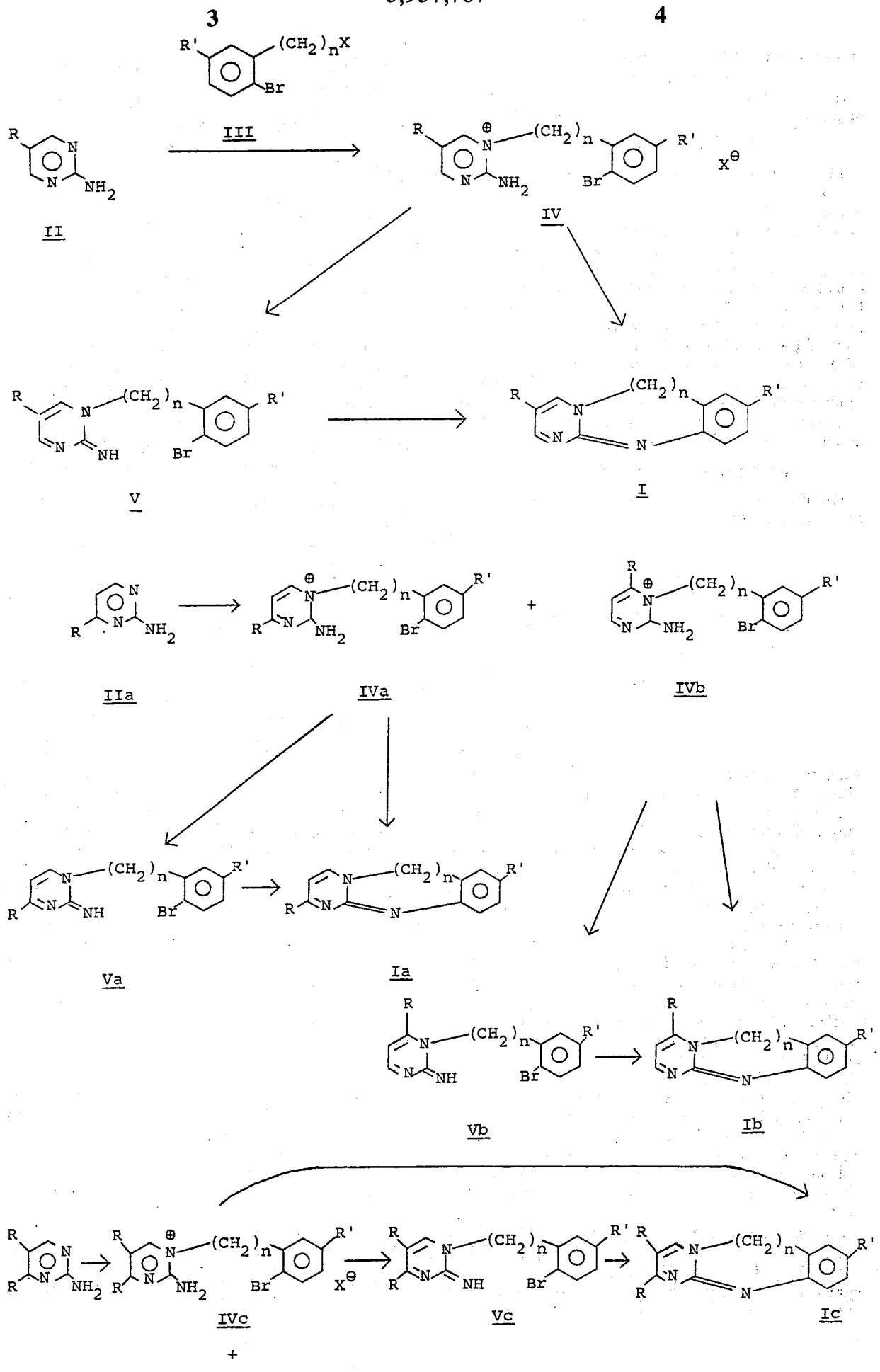

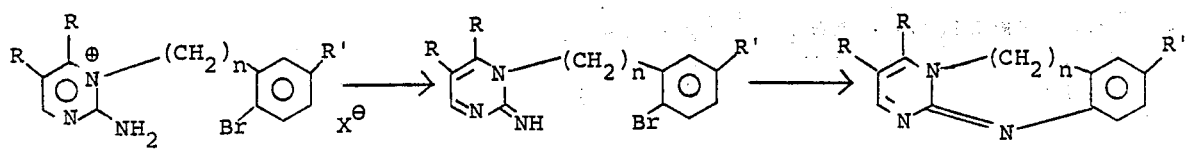

The intermediates of formula III wherein *n* is 2 may be prepared by treating an o-bromobenzyl alcohol VI with PBr₃ at temperatures of from about 0 to about 100°C for a period of from about 1 to about 6 hours. The resulting o-bromobenzyl bromide VII is then treated with sodium cyanide in the presence of water and a water miscible alcohol to yield an o-bromophenylacetonitrile VIII. Treatment of the latter with an alcohol in the presence of concentrated sulfuric acid yields the corresponding ester IX. Treatment of the latter with lithium aluminum hydride yields an o-bromophenethanol. Treatment of the latter with PBr₃ at temperatures within the range of from about 0° to about 100° for a period of from about 1 to about 6 hours yields the corresponding o-bromophenethyl bromide XI. The foregoing reaction sequence is illustrated by the following equations The intermediates of formula III wherein *n* is 3 may be prepared by treating a compound of formula XI with sodium cyanide in the presence of water and a water miscible alcohol to yield an o-bromophenylpropionitrile XII. Treatment of the latter with an alcohol in the presence of concentrated sulfuric acid yields the corresponding ester XIII. Treatment of the latter with lithium aluminum hydride yields an o-bromophenpropanol. Treatment of the latter with PBr₃ at temperatures within the range of from about 0° to about 100°C for a period of from about 1 to about 6 hours yields the corresponding o-bromophenpropyl bromide XV. The foregoing reaction sequence is illustrated by the following equations

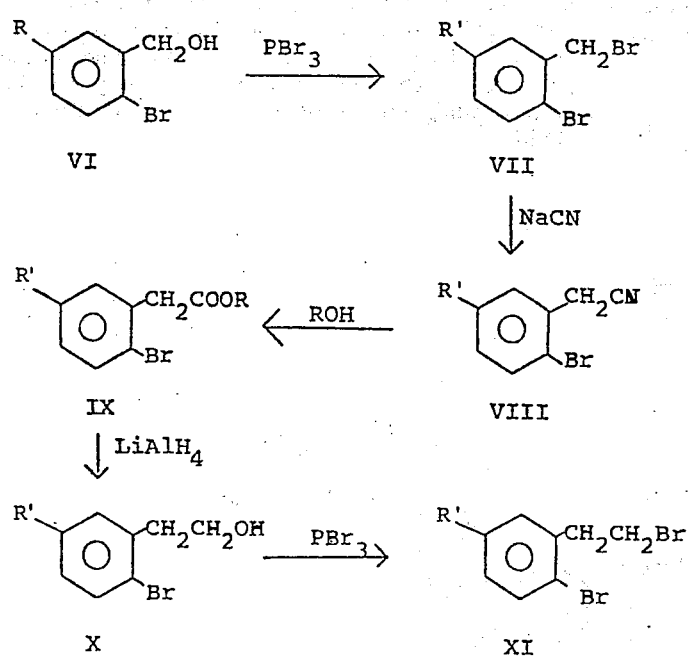

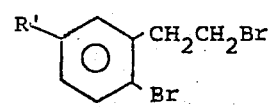

XIV                  XIII

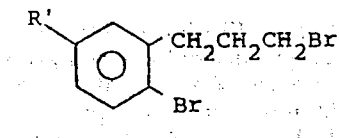

XV

When R' is alkylthio the compounds of formula XI or XV may be prepared by nitrating an o-bromobenzyl alcohol XVI at 0°C using a mixture of nitric and sulfuric acids. The resulting isomeric mixture of nitrated 2-bromobenzyl alcohols is separated by conventional techniques. Each separated isomer XVII may then be reduced to the corresponding amine XVIII by means of zinc and hydrochloric acid. Treatment of the amino derivative XVIII with nitrous acid and then with sodium alkylmercaptide yields the corresponding alkylthio-2-bromobenzyl alcohol XIX.

Treatment of the compound of formula XIX with $PBr_3$ as shown in the sequence proceeding from X to XI, and from XIV to XV yields the compound of formula XI or XV wherein R' is alkylthio.

When R' is trifluoromethyl, the intermediate of formula VII may be prepared by reacting a trifluoromethylphenyl magnesium bromide XX with methyl iodide to obtain a trifluoromethyl toluene XXI. Treatment of the latter with bromine in the presence of iron powder at 20°C yields a bromo-substituted trifluoromethyl toluene XXII. Treatment of the latter with bromine in the presence of light and a peroxide catalyst yields the corresponding bromo-trifluoromethylbenzyl bromide XXIII.

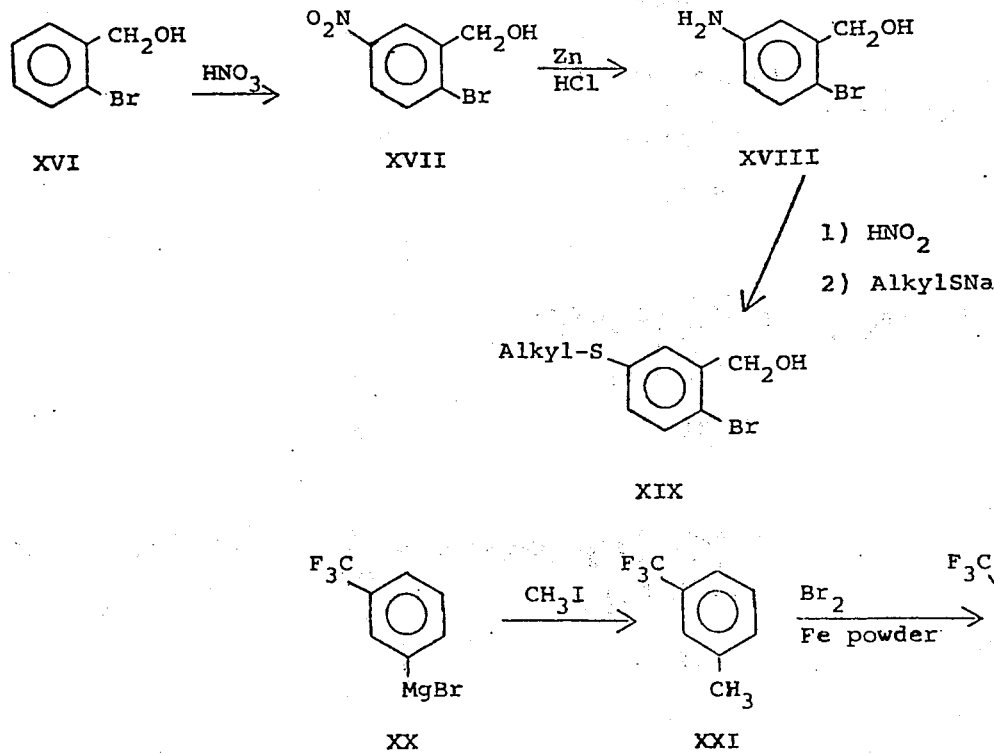

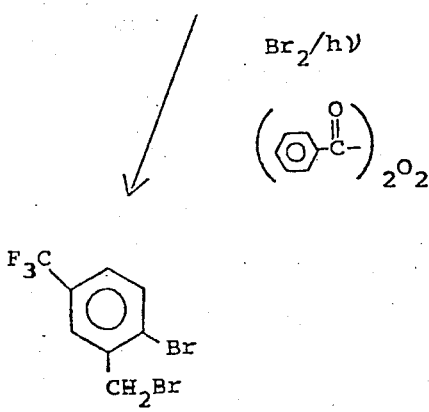

XXIII

Compounds of formula III wherein R' is phenyl, halogen-substituted phenyl, alkyl-substituted phenyl, alkoxy-substituted phenyl, or trifluoromethyl-substituted phenyl may be prepared by treating an amino-substituted o-bromobenzoic acid XXVIII with acetic anhydride and then with nitrous acid. The resulting N-acetamido-N-nitroso-o-bromobenzoic acid XXIX is then treated with benzene or an R-substituted benzene wherein R is halogen, alkyl, alkoxy or trifluoromethyl according to the procedure of Haworth et al, supra. The aryl-substituted o-bromobenzoic acid is then treated with LiAlH₄ or AlH₃ according to known techniques to yield the corresponding arylsubstituted o-bromobenzyl alcohol XXXI. The reaction sequence is as follows:

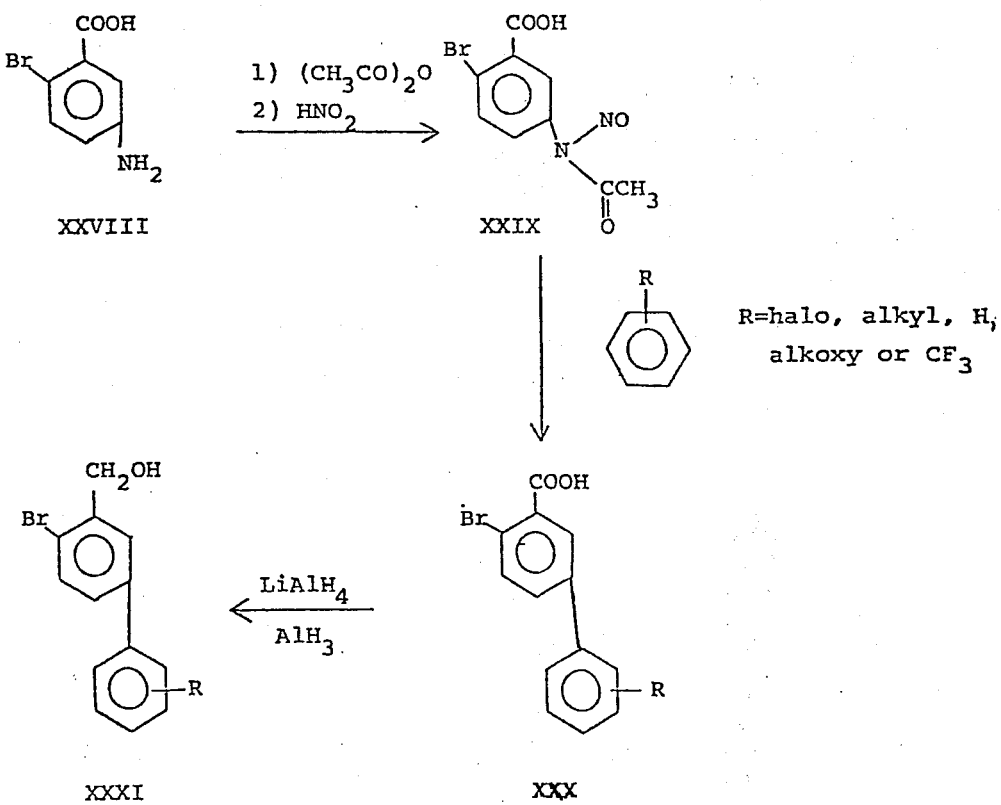

The compounds of the present invention may be administered to mammalian species as central nervous system stimulants and as muscle relaxants. In the rat, responses to the stimulant activity of the compounds of the present invention include increased activity and body tremors. The muscle relaxant properties manifest themselves by responses that include decreased limb tone, decreased grip strength, and limb paralysis. In both the stimulant and muscle relaxant activities, the onset of activity is rapid, i.e., within about 15 minutes; the activity persists for about 2 hours or longer. In the rat the dosage range varies from about 6.25 to about 50 mg/kg for both activities, while in humans the dosage range varies from about 40 to about 2000 mg. daily in about four divided doses for both activities.

In addition to serving as intermediates for the preparation of compounds of formula I, the pyrimidinium compounds of formula IV are themselves effective bactericides.

Microbial bioassays, as described in "The Microbial World," by R. Y. Stanier, M. Doudoroff and E. A. Adelberg, Prentice-Hall, Inc., Englewood Cliffs, N.J., 3rd Ed., p. 858, are employed to determine the bactericidal properties of the pyrimidinium compounds IV of this invention. The bacteria employed include *Staphylococcus aureus*, 1, *Streptococcus pyrogenes*, 2, *Salmonella schottmuelleri*, 3, *Salmonella gallinarum*, 4, *Pseudomonas aeruginosa*, 5, *Proteus vulgaris*, 6, *Escherichia coli*, 7, *Pasturella multocida*, 8, and *Mycobacterium tuberculosis*, 9.

In the procedure, a sterile agar plate is seeded with the test organism, and then a number of glass cylinders are placed on its surface, forming a series of little cups. A known dilution of the compounds of this invention is added to each cup and the entire plate is then incubated until significant bacterial growth has occurred. The compounds of this invention diffuse out of the cup into the surrounding agar and produce a zone of inhibition. In this fashion it is possible to find the minimum inhibiting concentration (mic), of the compound that produces a recognizable zone of inhibition. The following summarizes the data.

useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

As to the pharmaceutically acceptable salts, those coming within the purview of the invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic

| Microorganism | mic of Compound, Micrograms, (mcg)/ml | | | |
|---|---|---|---|---|
| | Compound of Ex. 3, col. 3 | Compound of Ex. 10, col. 3 | Compound of Ex. 12, col. 3 | Compound of Ex. 16 col. 3 |
| 1 | 12.5 | 6.25 | 6.25 | 3.13 |
| 2 | 50.0 | 50.0 | 25.0 | 12.5 |
| 3 | 50.0 | 12.5 | 12.5 | 12.5 |
| 4 | 25.0 | 12.5 | 12.5 | 6.25 |
| 5 | 25.0 | 25.0 | 25.0 | 12.5 |
| 6 | 25.0 | 25.0 | 25.0 | 12.5 |
| 7 | 25.0 | 12.5 | 6.25 | 3.13 |
| 8 | 12.5 | 25.0 | 12.5 | 6.25 |
| 9 | 6.25 | 1.57 | 0.78 | 0.39 |

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

The following examples illustrate the following invention without, however, limiting the same thereto. All temperatures are expressed in degrees Centigrade.

EXAMPLE 1

11,12-Dihydropyrimido[2,1-b][1,3]benzodiazepine

A. o-Bromobenzyl Bromide

To 187.0 g of o-bromobenzyl alcohol at room temperature, with stirring, is added dropwise, 271.0 g of phosphorus tribromide. After the addition is complete, stirring is continued for three hours at room temperature. The mixture is then heated at 90°–100° for three hours and poured into 6 kg of crushed ice. The hydrolysis mixture is extracted with three 600 ml portions of ether, the ether extracts are washed, dried, and concentrated to give o-bromobenzyl bromide, bp. about 130°–132° (15mm).

B. o-Bromophenylacetonitrile

To a suspension of 220.0 g of sodium cyanide in 265 ml of water and 380 ml of absolute ethanol, is added, while stirring, a solution of 911.0 g of o-bromobenzyl bromide in 911 ml of ethanol. The reaction proceeds exothermally, but is eventually heated under reflux for about 0.5 hour, then cooled in an ice-bath, and filtered. The solid is washed with ether, the filtrate is concentrated, the residue is suspended in 300 ml of water and extracted with three 500 ml portions of ether. The ether extracts are washed, dried, and the solvent is removed. The residue is distilled to give 730 g of the named product, bp 141°–142° (12mm).

C. Ethyl-o-bromophenylacetate

To a cooled solution of 730.0 g of o-bromophenylacetonitrile in 2.9 l of absolute ethanol is added, dropwise, while stirring, 740 ml of concentrated sulphuric acid. The addition requires about two hours. The reaction mixture is heated under reflux for nine hours, poured into ice water, and extracted with 2.5 l of ether. The ether extracts are washed, dried, and concentrated. The residue is distilled to give 780.0 g of ethyl o-bromophenylacetate, bp. about 115°–117° (4mm), $n_D^{26}$ 1,5434.

D. o-Bromophenethyl alcohol

To a stirred suspension of 106.0 g of lithium aluminum hydride in 3.7 l of anhydrous ether, is added, dropwise, a solution of 780.0 g of ethyl o-bromophenylacetate in 3.1 l of anhydrous ether. The reaction mixture is stirred for about three hours and then heated under reflux for about five hours. The mixture is cooled, then treated dropwise with 800 ml of water, and 1.5 l of 10% aqueous hydrochloric acid. The ether solution is washed, dried, concentrated, and the residue is distilled to give 554.0 g of o-bromophenethyl alcohol, bp. about 130°–132° (8mm), $n_D^{20}$ 1,5760.

E. o-Bromophenethyl bromide

To 550.0 g of o-bromophenethyl alcohol, while stirring, is added, dropwise, 375.0 g of phosphorus tribromide. After stirring for three hours at room temperature, the reaction mixture is heated on a steam bath for three hours and then poured into 6 kg of crushed ice. The mixture is extracted with three 600 and two 200 ml portions of ether. The ether extracts are washed, dried, concentrated, and the residue is distilled to give 531.0 g of o-bromophenethyl bromide, bp. about 86°–88° (0.9mm), $n_D^{26}$ 1.5922.

F. 2-Amino-1-(o-bromophenethyl)pyrimidinium Bromide

To a solution of 212.0 g of o-bromophenethyl bromide in 400 ml of dry xylene is added a solution of 121.0 g of 2-aminopyrimidine in 400 ml of dry xylene. The mixture is heated under reflux for about three hours, cooled, and the xylene solution is decanted from the crystalline solid. The solid is triturated with 300 ml of 2-propanol, filtered, and dried to give 138.0 g of the product. The xylene solution is again heated under reflux for 16 hours and by the same procedure, an additional 43.0 g of product is recovered. The total of about 181.0 g of product is recrystallized from 2-propanol to give 170.0 g of the title compound, mp. about 231°–232°.

G. 11,12-Dihydropyrimido[2,1-b][1,3]benzodiazepine

To a solution of 9.0 g of 2-amino-1-(o-bromophenethyl)pyridinium bromide in 55 ml of dimethylformamide is added 10.3 g of micronized, anhydrous potassium carbonate and 0.5 g of copper bronze. The mixture is heated at 100° for about seven days under nitrogen while stirring, and then is filtered while hot. The filtrate is concentrated to dryness in vacuo to give about 8.6 g of residue. This is extracted with two 125 ml portions of boiling diisopropyl ether. The diisopropyl ether solution is treated with Darco, filtered, and concentrated to about 40 ml to give on cooling, about 7.2 g of 11,12-dihydropyrimido[2,1-b][1,3]benzodiazepine, mp about 45°–46°.

EXAMPLE 2

12,13-Dihydro-2-methylthio-11H-pyrimido[2,1-b][1,3]-benzodiazocine

A. 2-Bromo-5-methylthiobenzyl Bromide

2-Bromo-5-methylthiobenzyl alcohol is prepared by the following sequence of reactions: 2-bromo-5-nitrobenzoic acid is reduced to 2-bromo-5-aminobenzoic acid by means of iron and hydrochloric acid in aqueous ethanol. The 2-bromo-5-aminobenzoic acid is diazotized with sodium nitrite in aqueous sulfuric acid, and the diazonium compound treated with sodium methylmercaptide to give 2-bromo-5-methylthiobenzoic acid. The 2-bromo-5-methylthiobenzoic acid is converted to its methyl ester by heating under reflux with methanol-concentrated sulfuric acid, the methyl ester is isolated by ether extraction from the esterification mixture, recovered from the ether solution, distilled for purification, and reduced with lithium aluminum hydride to yield 2-bromo-5-methylthiobenzyl alcohol. Treatment of the preceding compound with $PBr_3$ as described in part A of example 1 gives 2-bromo-5-methylthiobenzyl bromide.

B. 3-(2-Bromo-5-(methylthio)phenyl)-1-propanol

To a suspension of 25.0 g of magnesium ribbon in a solution of 0.5 g of iodine in 550 ml of anhydrous ether is added 5 ml of a solution of 296.0 g of 2-bromo-5-(methylthio)benzyl bromide in 250 ml of anhydrous ether. The reaction is initiated by gentle heating, and the remainder of the solution is then added dropwise so as to maintain a reflux. Subsequently, the mixture is heated and stirred under reflux for one hour, and then cooled to 10°. A stream of nitrogen gas that has been bubbled through a reservoir containing 48.0 g of ethylene oxide is introduced into the reaction mixture. The addition of the ethylene oxide requires two hours. The mixture is subsequently stirred as it warms to room temperature, is stirred for four hours at room temperature, and then hydrolyzed by pouring on a mixture of 1 kg of ice and 55.0 g of ammonium chloride. Extraction with ether, followed by conventional workup of the ether solution, yield 210.0 g of 3-(2-bromo-5-(methylthio)phenyl)-1-propanol, bp, about 125°–127° (0.6mm).

C. 3-(2-Bromo-5-methylthiophenyl)propyl Bromide

To 49.0 g of the product from (A), with stirring, is added, dropwise, 27.1 g of phosphorus tribromide. The mixture is stirred subsequently for three hours at room temperature, then heated at 90°–100° for three hours, and then poured into 1 kg of crushed ice. Workup via ether extraction yields 52.7 g of 3-(2-bromo-5-methylthiophenyl)propyl bromide, bp. about 100°–102° (0.8mm).

D.
2-Amino-1-[3-(2-bromo-5-methylthiophenyl)propyl]-pyrimidinium bromide

To a solution of 154.0 g of 3-(2-bromo-4-methylthiophenyl)propyl bromide in 400 ml of dry xylene, is added a solution of 70.0 g of 2-aminopyrimidine in 300 ml of dry xylene and the mixture is heated under reflux for about 18 hours. The cooled xylene solution is decanted from the crystalline solid, the solid is triturated with 200 ml of 2-propanol and filtered to give 117.0 g of crude product. Recrystallization of the latter from 2-propanol gives about 98.0 g of 2-amino-1-[3-(2-bromo-4-methylthiophenyl)propyl]-pyrimidinium bromide.

E.
12,13-Dihydro-2-methylthio-11H-pyrimido[2,1-b][1,3]-benzodiazocine

To a solution of 8.1 g of 2-amino-1-[3-(2-bromo-5-methylthiophenyl)propyl pyrimidinium bromide] in 50 ml of dimethylformamide is added 10.3 g of micronized, anhydrous potassium carbonate and 0.5 g of copper bronze. The mixture is heated at 100° for about three hours under nitrogen while stirring, and then it is filtered hot. The filtrate is concentrated to dryness in vacuo to give about 9.0 g of residue. This is extracted with two 120 ml portions of boiling diisopropyl ether. The solution is treated with Darco, filtered, and concentrated to about 35 ml. This on cooling gives about 4.3 g of 12,13-dihydro-2-methylthio-11H-pyrimido[2,1-b][1,3]-benzodiazocine.

EXAMPLES 3–17

Following the procedure of example 1 (A) but substituting an equivalent amount of the substituted o-bromobenzyl alcohol in column 1 for o-bromobenzyl alcohol, there is obtained respectively, the corresponding o-bromophenethyl bromide indicated in column 2. Reaction of the latter with 2-aminopyrimidine following the procedure of example 1 (F) yields, respectively, the pyrimidinium compound indicated in column 3. Treating the latter with $K_2CO_3$ and copper bronze following the procedure of example 1 (G) yields, respectively, the final product of column 4.

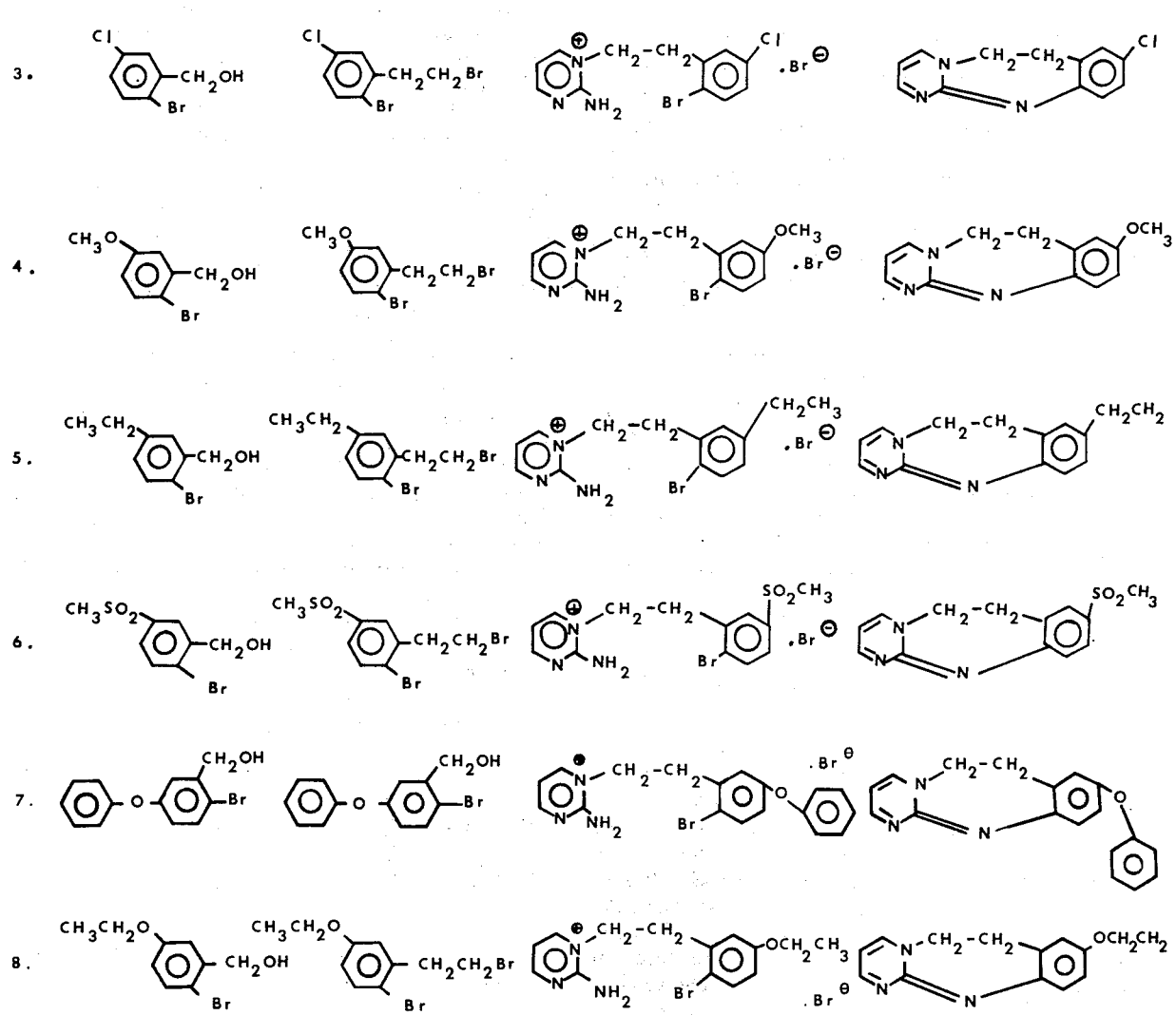

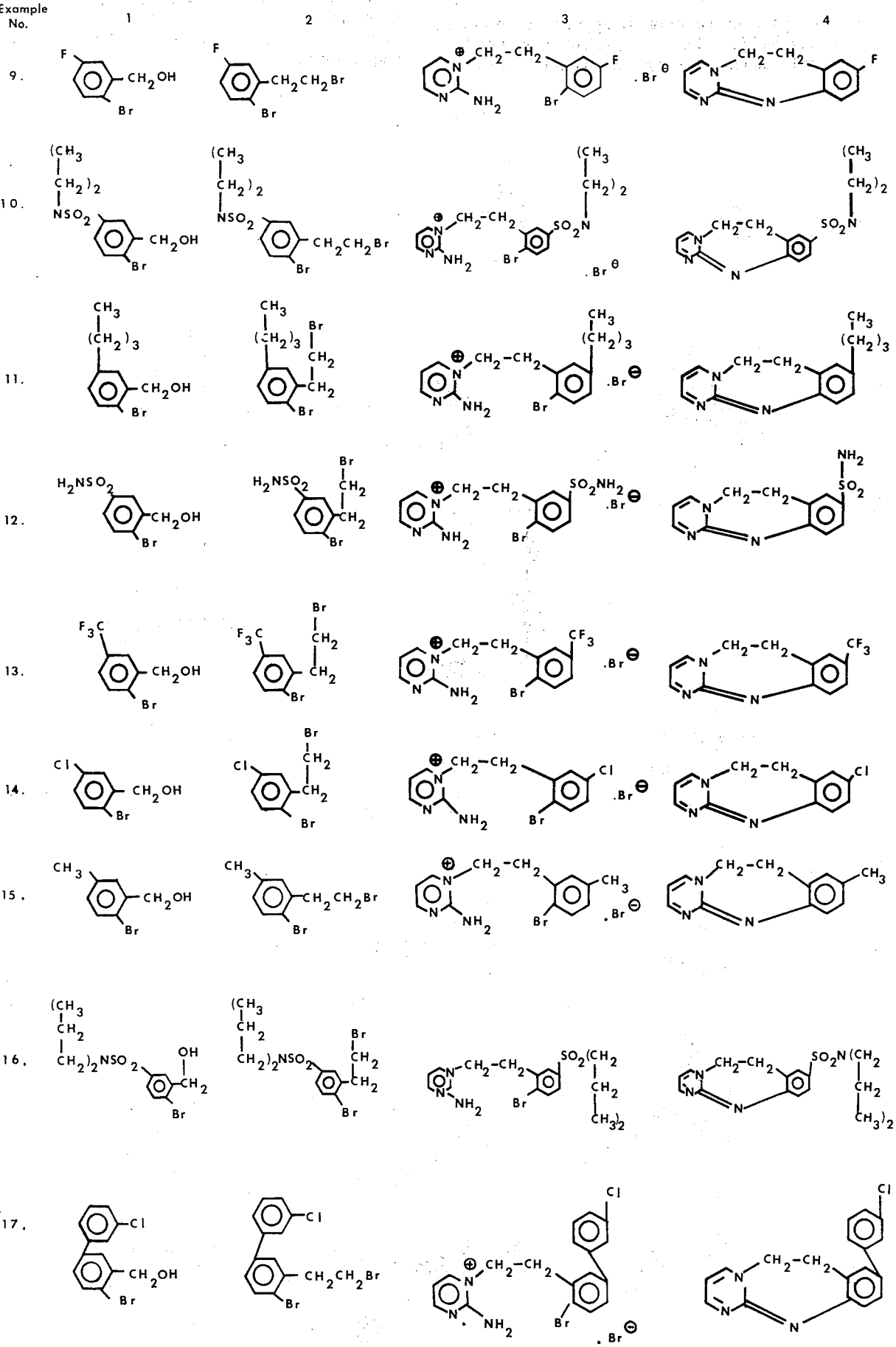

EXAMPLES 18–30
Following the procedure of example 1, but substituting for 2-aminopyrimidine an equivalent amount of the substituted 2-aminopyrimidine in column 1, there is obtained, respectively, the quaternary derivative shown in column 2. Treatment of the latter as described in example 1 yields, respectively, the final compound indicated in column 3.
| Example No. | 1 | 2 | 3 |
|---|---|---|---|
| 18. | 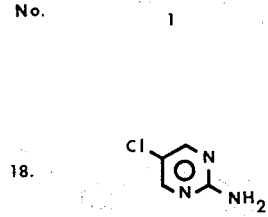 | 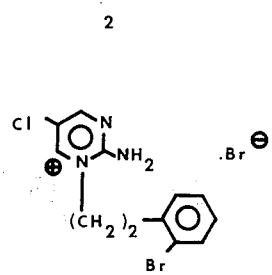 | 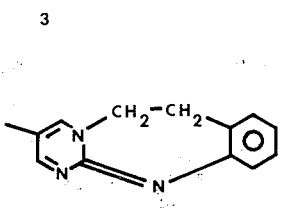 |
| 19. | 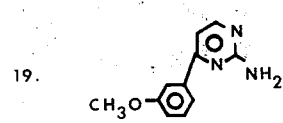 | 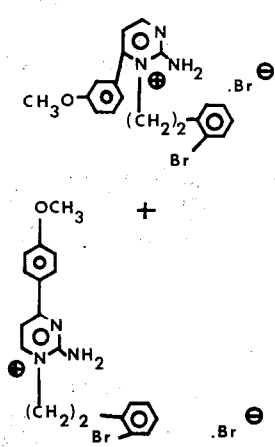 | 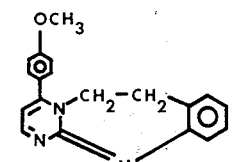 |
| | | + | + |
| | | | 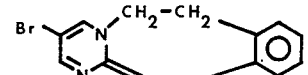 |
| 20. | 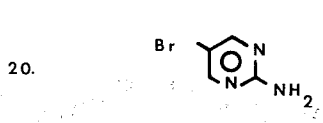 | 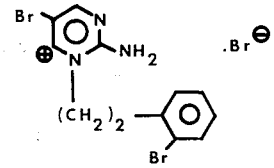 | |
| 21. | 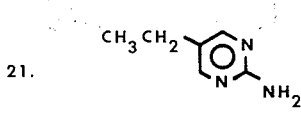 | 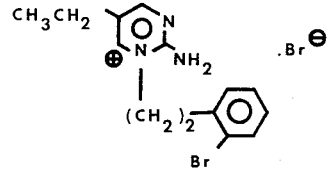 | 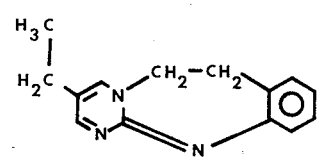 |
| 22. | 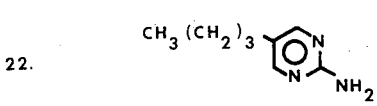 | 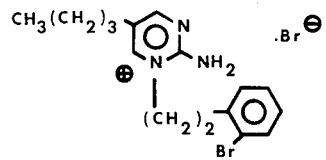 | 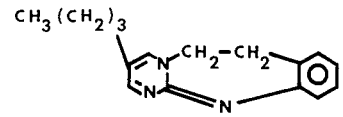 |
| 23. | 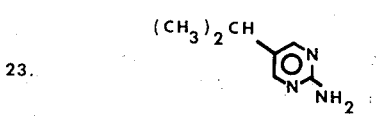 | 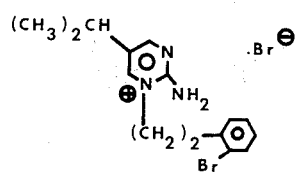 | 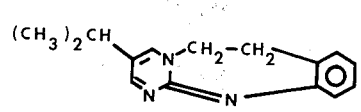 |

-continued
| Example No. | 1 | 2 | 3 |
|---|---|---|---|
| 24. | 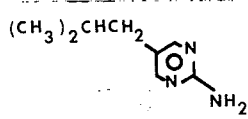 | 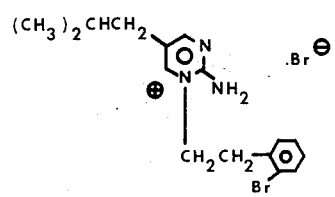 | 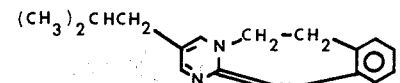 |
| 25. | 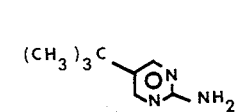 | 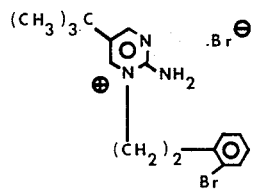 | 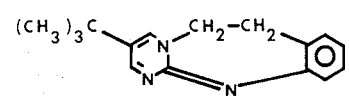 |
| 26. | 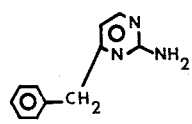 | 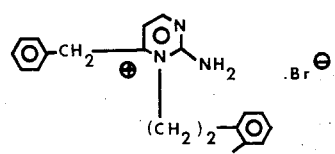 <br> + <br> 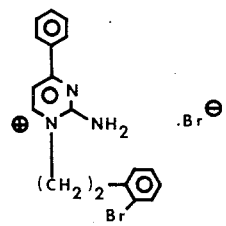 | 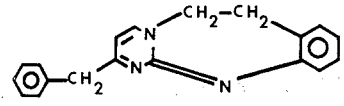 <br> + <br> 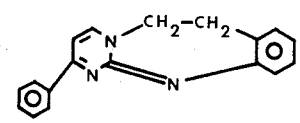 |
| 27. | 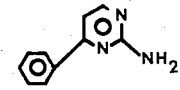 | 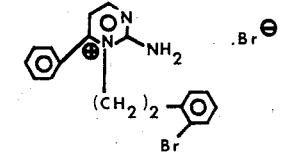 <br> + <br> 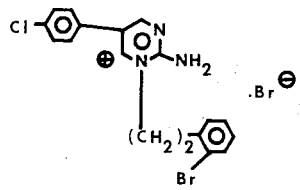 | 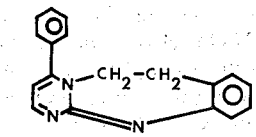 <br> + <br> 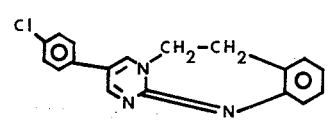 (partial) |
| 28. | 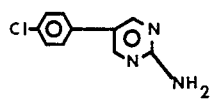 | | |

| Example No. | 1 | 2 | 3 |
|---|---|---|---|
| 29. | 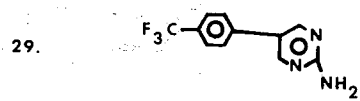 | 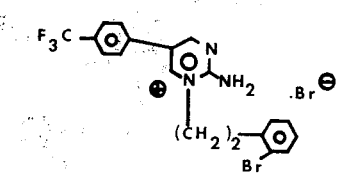 | 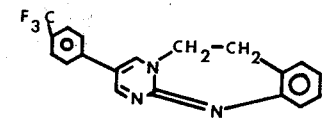 |
| 30. | 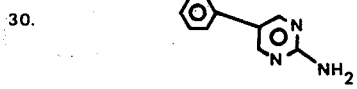 | 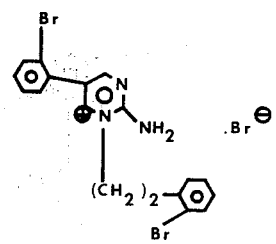 | 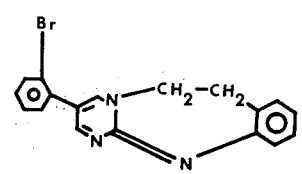 |

EXAMPLE 31

11,12-Dihydropyrimido[2,1-b][1,3]benzodiazepine

To a solution of 18.0 g of 2-amino-1-(o-bromophenethyl)pyrimidinium bromide and 14.7 g of potassium carbonate in 100 m/ of n-propanol and 200 ml of water is added 0.5 g of copper bronze and the mixture is heated under nitrogen, with stirring, at 90° for 2.5 hours. The mixture is cooled and extracted with three 100 ml portions of ether, the ether extracts are washed, dried, and concentrated to give about 10.0 g of product, mp about 45°–46°, after recrystallization from diisopropyl ether.

EXAMPLE 32

A.
1,2-Dihydro-2-imino-1-(o-bromophenethyl)pyrimidine

To a solution of 3.3 g of sodium methoxide in 120 ml of anhydrous methanol is added 10.8 g of 2-amino-1-(o-bromophenethyl)pyrimidinium bromide, prepared as described in example 1 (G). The solution is stirred under nitrogen for 2 hours and then heated under reflux for 5 hours. The solvent is removed in vacuo and the residue is treated with 200 ml of anhydrous ether.

The ether solution is washed, dried, and concentrated in vacuo to give about 6.8 g of yellow solid. This is recrystallized from hexane to give the name product, mp about 97°–98°.

B. 11,12-Dihydropyrimido[2,1-b][1,3]benzodiazepine

To a solution of 5.6 g of 1,2-dihydro-2-imino-1-(o-bromophenethyl)pyrimidine in 100 ml of xylene is added 2.8 g of potassium carbonate and 0.5 g of copper bronze and the mixture is heated under reflux for 3 hours, and filtered. The filtrate is concentrated in vacuo and the residue recrystallized from diisopropyl ether to give about 2.3 g of the title product, mp about 45°–46°.

EXAMPLES 33–35

Following the procedure of example 1 (B) through 1 (G) but substituting the o-bromophenethylbromide in column I below for the o-bromobenzyl bromide in part B, and substituting for 2-aminopyrimidine in part F, the compound listed in column II, there is obtained (from part F) the pyrimidinium compound listed in column III and (from part G) the benzodiazocine compound listed in column IV.

| Example No. | I | II |
|---|---|---|
| 33. | 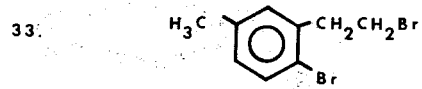 | 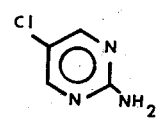 |
| 34. | 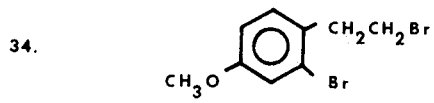 | 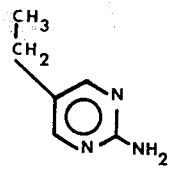 |
| 35. | 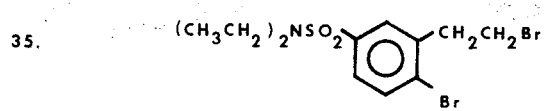 | 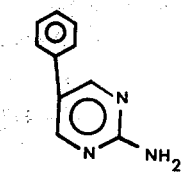 |

| Example No. | III | IV |
|---|---|---|
| 33. | 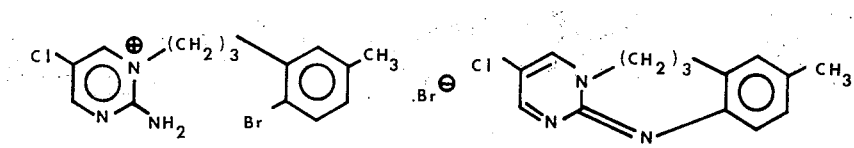 | |
| 34. | 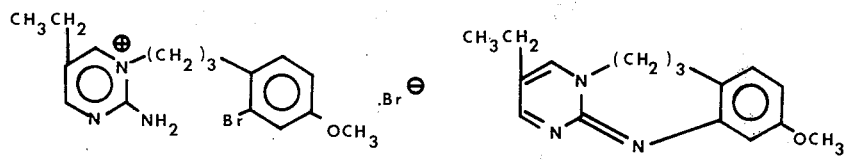 | |
| 35. | 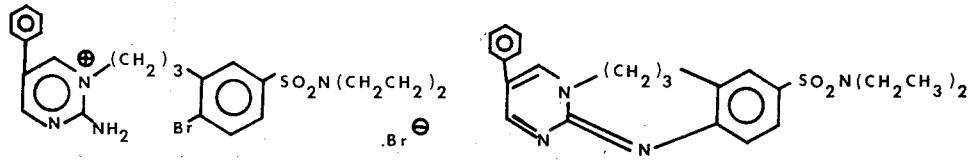 | |

EXAMPLES 36–39

Following the procedure of example 1 but substituting for 2-aminopyrimidine an equivalent amount of the substituted 2-aminopyrimidine in column 1, there is obtained, respectively, the quaternary derivative shown in column 2. Treatment of the latter as described in example 1 yields, respectively, the final compound indicated in column 3.

| Example No. | I | II | III |
|---|---|---|---|
| 36. | 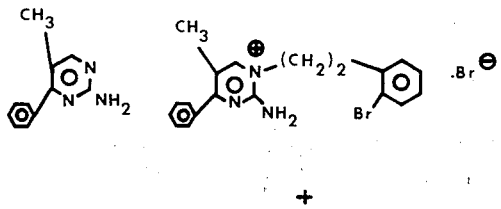 | 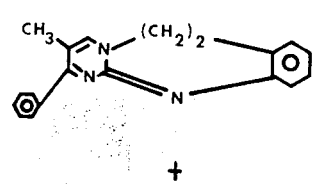 | |
|  | | + | + |
|  | | 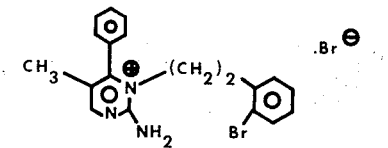 | |
| 37. | 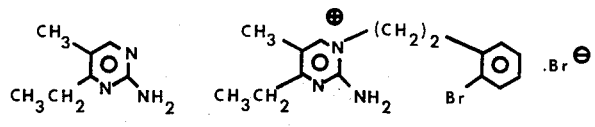 | 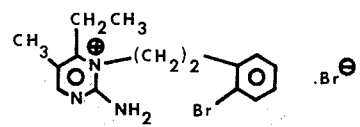 | 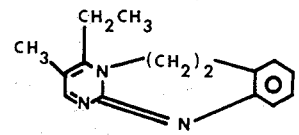 |

EXAMPLES 40–51

Following the procedure of example 1 (B) through 1 (G) but substituting for o-bromobenzyl bromide in part B, the compound listed in column I below, and substituting for 2-aminopyrimidine in part F, the compound listed in column II, there is obtained (from part F) the pyrimidinium compound listed in column III and from part G the benzodiazepine compound listed in column IV.

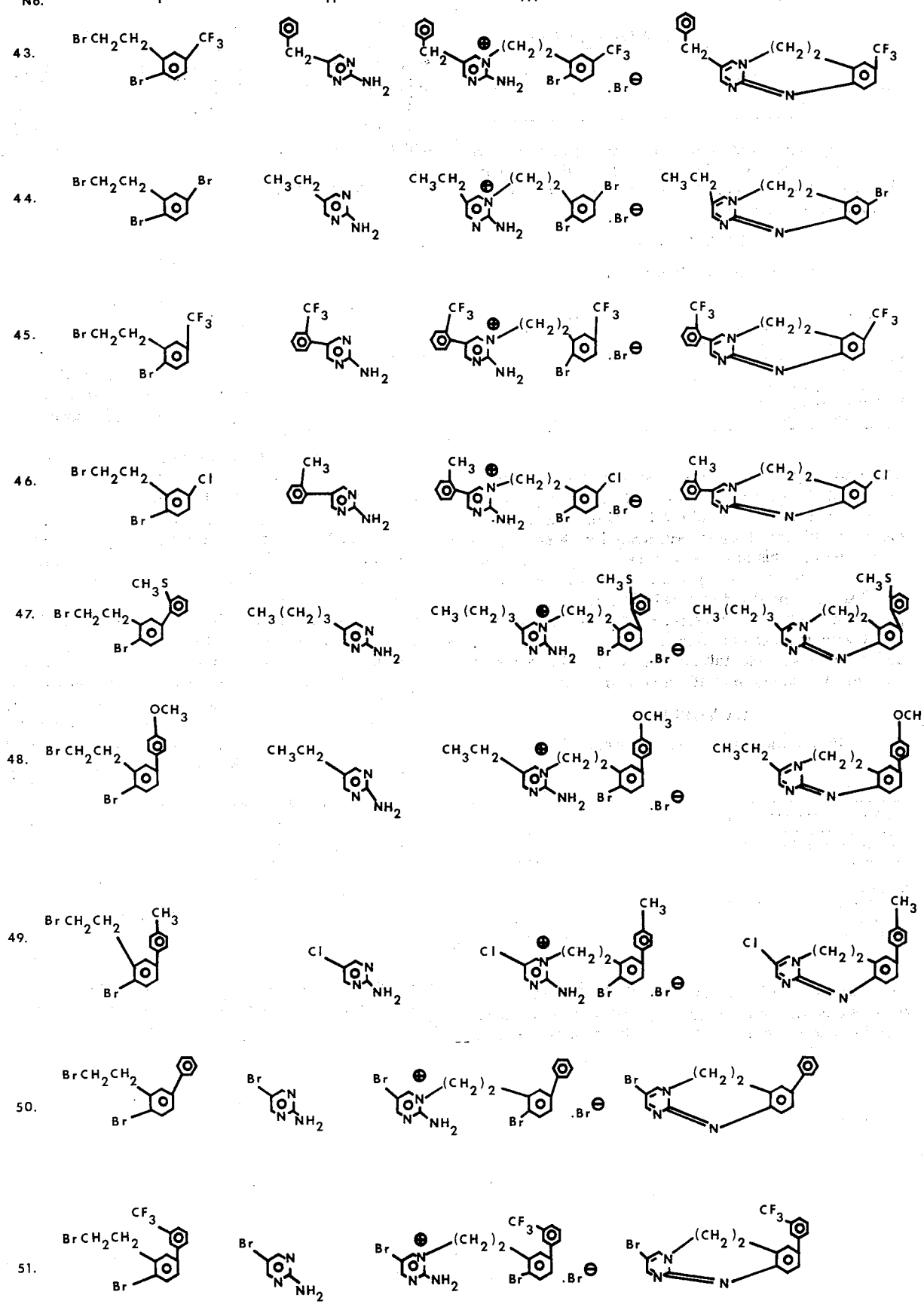

EXAMPLE 52

Preparation of capsule formulation

| Ingredient | Milligrams per Capsule |
|---|---|
| 11,12-Dihydropyrimido-[2,1-b][1,3]benzodiazepine | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 53

Preparation of tablet formulation

| Ingredient | Milligrams per Tablet |
|---|---|
| 12,13-Dihydro-2-methylthio-11H-pyrimido[2,1-b][1,3]benzodiazocine | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 54

Preparation of oral syrup formulation

| Ingredient | Amount |
|---|---|
| 11,12-Dihydropyrimido[2,1-b]-[1,3]benzodiazepine | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water | qs. to 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. An intermediate of the formula

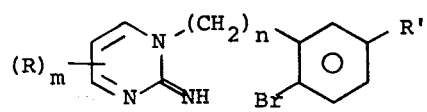

wherein m is 1 or 2; when m is 1, R occupies either the 4- or 5-positions of the starting 2-aminopyrimidine, but when R is halogen it occupies only position-5; when m is 2, the two R-substituents occupy the 4- and 5-positions of the starting 2-aminopyrimidine, but only one of the two R-substituents can be halogen and it must occupy the 5-position;

R is the same or different and is hydrogen, F, Cl, Br, alkyl of from 1 to 4 carbons, benzyl, phenyl, or mono-substituted phenyl wherein the substituent is F, Cl, Br, I, alkyl of from 1 to 4 carbons, or trifluoromethyl;

R' is hydrogen, F, Cl, Br, I, alklyl of from 1 to 4 carbons, alkoxy of from 1 to 4 carbons, alkylthio of from 1 to 4 carbons, alkylsulfonyl wherein the alkyl radical has from 1 to 4 carbons, phenyl, phenyloxy, sulfamoyl, dialkylamidosulfonyl wherein each alkyl radical has from 1 to 4 carbons, trifluoromethyl, mono-substituted phenyl or mono-substituted phenyloxy wherein the substituent is F, Cl, Br, I, alkyl of from 1 to 4 carbons, alkoxy of from 1 to 4 carbons or trifluoromethyl; n is 2 or 3.

2. An intermediate for a compound as defined in claim 1 of the formula

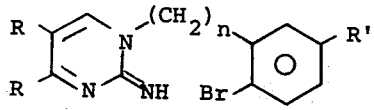

wherein R, n and R' are as defined in claim 1.

3. A compound of claim 1 having the name 1,2-dihydro-2-imino-1-(o-bromophenethyl)pyrimidine.

* * * * *

UNITED STATES PATENT AND TRADEMARK OFFICE
CERTIFICATE OF CORRECTION

PATENT NO. : 3,957,787
DATED : May 18, 1976
INVENTOR(S) : Harry Louis Yale

It is certified that error appears in the above-identified patent and that said Letters Patent are hereby corrected as shown below:

Column 23, line 30, "m/" should read --ml--.
Column 32, line 32, before the word "or", insert
   --alkoxy of from 1 to 4 carbons--.

Signed and Sealed this

Twenty-first Day of September 1976

[SEAL]

*Attest:*

RUTH C. MASON
*Attesting Officer*

C. MARSHALL DANN
*Commissioner of Patents and Trademarks*